United States Patent [19]

Menard et al.

[11] Patent Number: 4,723,049
[45] Date of Patent: Feb. 2, 1988

[54] TOLUENE DISPROPORTIONATION PROCESS

[75] Inventors: Kevin P. Menard, Big Spring; Eugene W. Cotten, Jr., Beaumont, both of Tex.

[73] Assignee: Cosden Technology, Inc., Dallas, Tex.

[21] Appl. No.: 51,492

[22] Filed: May 18, 1987

[51] Int. Cl.$^4$ ................................................ C07C 3/62
[52] U.S. Cl. .................................................... 585/475
[58] Field of Search ......................................... 585/475

[56] References Cited

U.S. PATENT DOCUMENTS

| | | |
|---|---|---|
| 3,436,174 | 4/1969 | Sand . |
| 3,476,821 | 11/1969 | Brandenburg et al. . |
| 3,480,539 | 11/1969 | Voorhies et al. . |
| 3,780,122 | 12/1973 | Pollitzer . |
| 3,915,895 | 10/1975 | Suggitt et al. . |
| 4,665,258 | 5/1987 | Butler et al. ........................ 585/475 |

OTHER PUBLICATIONS

Kirk-Othmer, Encyclopedia of Chemical Technology, 3rd Edition, John Wiley & Sons, 1981, "Molecular Sieves", vol. 15, pp. 638-643.

Bhavikatti et al, "Toluene Disproportionation over Aluminum-Deficient and Metal-Loaded Mordenites. 1. Catalytic Activity and Aging", Ind. Eng. Chem. Prod. Res. Dev., 1981, 102-105.

*Primary Examiner*—Curtis R. Davis
*Attorney, Agent, or Firm*—William D. Jackson; John K. Abokhair; M. Norwood Cheairs

[57] ABSTRACT

A process for the disproportionation of a toluene containing feedstock over an aluminum deficient mordenite catalyst having a silica/alumina mole ratio of at least 30. The feedstock and hydrogen co-feed are supplied to a reaction zone containing the mordenite catalyst and which is operated under a temperature and pressure condition to effect the disproportionation of toluene to benzene and xylene. The supply of toluene feedstock to the reaction zone is interrupted while continuing the supply of hydrogen to the reaction zone. By continuing the supply of hydrogen to the reaction zone during periods of interruption of the toluene feedstock, the aging quality of the aluminum-deficient mordenite catalyst is improved.

10 Claims, 1 Drawing Figure

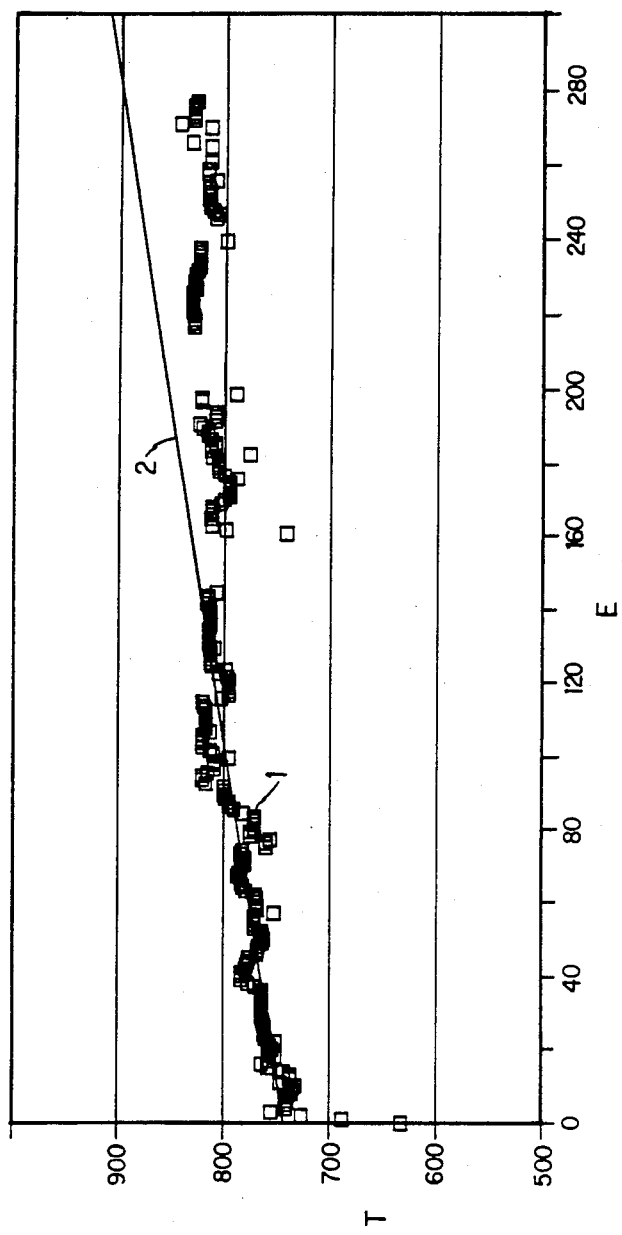

TOLUENE DISPROPORTIONATION PROCESS

TECHNICAL FIELD

This invention relates to the disproportionation of alkylaromatic feedstreams and more particularly to the disproportionation of toluene containing feedstocks employing mordenite catalysts of low aluminum content.

ART BACKGROUND

The disproportionation of toluene involves a well known transalkylation reaction in which toluene is converted to benzene and xylene in accordance with the following reaction:

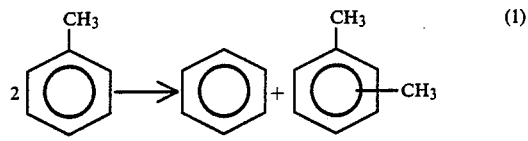

Reaction (1) is mildly exothermic.

Mordenite is one of a number of catalysts commonly employed in the transalkylation of alkylaromatic compounds. Mordenite is a crystalline aluminosilicate zeolite having a network of silicon and aluminum atoms interlinked in its crystalline structure through oxygen atoms. For a general description of mordenite catalysts, reference is made to Kirk-Othmer *Encyclopedia of Chemical Technology*, 3rd Edition, 1981, under the heading "Molecular Sieves", Vol. 15, pages 638–643. Mordenite, as found in nature or as synthesized, typically has a relatively low silica to alumina mole ratio of about 10 or less. Such conventionally structured mordenite catalysts are commonly employed in the disproportionation of toluene. However, mordenite catalysts having substantially lower alumina content are also employed in the disproportionation of toluene.

The aluminum deficient mordenite catalysts have a silica/alumina ratio greater than 10 and may sometimes range up to about 100. Such low alumina mordenites may be prepared by direct synthesis as disclosed, for example, in U.S. Pat. No. 3,436,174 to Sand or by acid extraction of a more conventionally prepared mordenite as disclosed in U.S. Pat. No. 3,480,539 to Voorhies et al.

U.S. Pat. No. 3,780,122 to Pollitzer discloses the transalkylation of toluene using a mordenite zeolite having a silica/alumina ratio greater than 10 which is obtained by acid extraction of a mordenite zeolite having a silica/alumina ratio of less than 10. The silica/alumina ratio may range up to about 100 and preferably is at least about 15. The yield in the Pollitzer process is severely affected by water in the toluene feedstock. As shown in Table II, even a very small amount of water (15 ppm) reduces toluene conversion substantially and the patent designates an upper limit of 25 ppm water in the feedstock.

The disproportionation of toluene feedstocks may be carried out at temperatures ranging from about 200° C. to about 600° C. or above and at pressures ranging from atmospheric to perhaps 100 atmospheres or above. However, the catalyst itself may impose constraints on the reaction temperatures in terms of catalyst activity and aging characteristics. In general, the prior art indicates that while relatively high temperatures can be employed for the high aluminum mordenites (low silica to alumina ratios) somewhat lower temperatures should be employed for the low alumina mordenites. Thus, where mordenite catalysts having high silica/alumina ratios have been employed in the transalkylation of alkylaromatics, it has been the practice to operate toward the lower end of the temperature range. It is also a common practice in this case to promote the catalyst with a catalytically active metallic content. For example, U.S. Pat. No. 3,476,821 to Brandenburg et al discloses disproportionation reactions employing mordenite catalysts having a silica/alumina ratio within the range of 10–100 and preferably within the range of about 20–60. Here desired temperature ranges are said to be from about 400°–750° F. and preferably 450°–640° F. Metal promoters are said to substantially increase activity and catalyt life.

It is conventional practice to supply hydrogen along with toluene to the reaction zone. While the disproportionation reaction (1) is net of hydrogen, the use of a hydrogen co-feed is generally considered to prolong the useful life of the catalyst, as disclosed, for example, in the above patent to Brandenburg. The amount of hydrogen supplied, which normally is measured in terms of the hydrogen/toluene mole ratio, is generally shown in the prior art to increase as temperature increases. For example, while the patent to Pollitzer discloses a range for the hydrogen/toluene mole ratio of 2–20 corresponding to the broad temperature range of 200°–480° C., the specific examples in Pollitzer of operating at temperatures ranging from 300°–400° C. employ a hydrogen/toluene mole ratio of 10.

The use of mordenite catalysts of high silica/alumina ratio in toluene disproportionation is also disclosed in U.S. Pat. No. 3,915,895 to Suggitt et al. The silica/alumina mole ratios proposed in Suggitt range from 10 to about 100 (preferably 12–80 and more preferably about 25 to 50). The catalysts for which experimental information is given in Suggitt had silica/alumina ratios of 18 and 39. At the disproportionation conditions employed (550° F. and 200 or 800 psig.), neither catalyst showed particularly good activity although the higher alumina catalyst promoted with silver was better than the unpromoted catalyst.

Bhavikatti et al, "Toluene Disproportionation over Aluminum-Deficient and Metal-Loaded Mordenites. 1. Catalytic Activity and Aging", Ind. Eng. Chem. Prod. Res. Dev. 1981, 20, 102–105, discloses toluene disproportionation at 400° C. over mordenite catalysts of silica/alumina mole ratios of 12, 16, 23, 32, and 61. The tests reported in Bhavikatti were carried out at atmospheric pressure and with a WHSV of 1. As the silica/alumina mole ratio is increased, catalyst activity substantially decreased while aging quality increased. That is, the aging rates were lower. Based upon short term aging studies, the best silica/alumina mole ratio appeared to be 23. Catalyst decay was also supressed by loading the mordenite with nickel.

U.S. patent application Ser. No. 826,848 filed Feb. 6, 1986, by James R. Butler and Kevin P. Menard discloses disproportionation of a toluene containing feedstock employing an aluminum deficient mordenite catalyst under relatively severe disproportionation conditions. The mordenite catalyst has a silica/alumina mole ratio of at least 30 and preferably a silica/alumina ratio within the range of 40–60. The feedstock may be supplied to a reaction zone containing the mordenite catalyst at rates providing relatively high space velocities. The toluene weight hourly space velocity (WHSV) may be greater than 1. Hydrogen is also supplied to the reaction zone at a rate to provide a hydrogen/toluene mole ratio within the range of 3–6. The reaction zone is operated at a temperature in the range of 370°–500° C. and a hydrogen pressure of at least 500 psig to effect disproportionation of the toluene to benzene and xylenes. More specific reaction conditions include a temperature within the range of 400°–480° C., a hydrogen pressure of about 600–800 psig, and a mole ratio of hydrogen to toluene of about 4. The preferred catalyst is hydrogen mordenite having a silica/alumina ratio of about 48.

The toluene feedstock used in the process of application Ser. No. 826,848 need not be dried before supplying it to the reaction zone. Thus, toluene feedstock having a water content in excess of 25 ppm can be applied directly into the reaction zone. The Butler et al application further discloses passing a preflush gas to the reaction zone prior to initiating the disproportionation reaction. The preflush gas is heated to a temperature sufficient to strip water from the catalyst so that it is substantially dehydrated by the time the toluene feed is started. This enables the disproportionation process to be carried out initially at a somewhat lower temperature without a reduced toluene conversion than would otherwise be the case. As the disproportionation process continues, the temperatures progressively increase to maintain the toluene conversion at the desired level, typically about 80% of theoretical.

DESCRIPTION OF THE INVENTION

In accordance with the present invention, there is provided a new and improved process for the disproportionation of toluene over an aluminum deficient mordenite catalyst in which catalyst activity and aging quality are enhanced. In carrying out the invention, a toluene containing feedstock is supplied to a reaction zone containing a mordenite catalyst having a silica/alumina ratio of at least 30. Hydrogen is also supplied to the reaction zone to provide a hydrogen environment, and the reaction zone is operated under temperature and pressure conditions to effect the disproportionation of toluene to benzene and xylene. The disproportionation product containing these compounds is withdrawn from the reaction zone. In the course of the disproportionation process, the supply of the toluene feedstock to the reaction zone is interrupted, but the supply of hydrogen is continued while hydrogen is withdrawn from the reaction zone. Preferably, the hydrogen is supplied to and withdrawn from the reaction zone for a period of at least one day before reinstating the supply of toluene feedstock to the reaction zone. By thus maintaining a hydrogen environment over the mordenite catalyst during shutdown periods of the disproportionation process, the aging quality of the catalyst is increased, and in addition, an improvement in activity for a given set of disproportionation conditions is generally observed. Preferably, the reaction zone is operated at a temperature within the range of 370°–500° C. during the supply of toluene feedstock and is maintained at a temperature of at least 250° C. when hydrogen is supplied during periods of feedstock interruption.

BRIEF DESCRIPTION OF THE DRAWING

The drawing is a graph illustrating the reactor inlet temperature plotted as a function of time for a toluene disproportionation process carried out with interruptions in the supply of toluene feedstock.

BEST MODES FOR CARRYING OUT THE INVENTION

As noted previously, the aforementioned application Ser. No. 826,848 by Butler et al presents a substantial departure from practices previously followed in disproportionating toluene feedstocks over aluminum deficient mordenite catalysts. The present invention provides an improved mode of carrying out toluene disproportionation processes over a high silica/alumina ratio mordenite catalyst as disclosed in the Butler et al application, and except for periods of interruption as discussed below, the present invention may be carried out in accordance with the process parameters and procedures described in the aforementioned Butler et al application.

Thus, the reaction zone is normally operated at a temperature within the range of 370°–500° C. Preferably, the reaction zone temperature is 400°–500° C. The mordenite catalyst employed in the present invention should have a silica/alumina ratio of at least 30 and preferably within the range of 40–60. The catalyst need not be promoted. Hydrogen normally is also supplied to the reaction zone to provide a hydrogen pressure within the zone of at least 500 psig. Unless indicated otherwise, all pressures given herein are hydrogen pressures or in the case of a hydrogen feed containing other gases, hydrogen partial pressures. For example, in the case of a gas containing 90% hydrogen and 10% other gases such as light hydrocarbons and nitrogen, the reaction zone should be operated at a pressure of about 555 psig to yield a hydrogen presure of 500 psig. The pressure at which the disproportionation reaction is carried out normally will be within the range of about 600–800 psig. Lower pressures may be employed, but will result in lower toluene conversion unless higher temperatures are used, which will decrease the catalyst cycle life. Preferably, the reaction zone for the toluene disproportionation reaction will be at a pressure of about 600 psig or above.

The aforementioned temperature and pressure conditions permit the use of lower than normal hydrogen amounts and higher than normal space velocities. The specific parameters employed in this regard include a toluene space velocity (WHSV) in excess of 1 $hr^{-1}$ and a hydrogen/toluene mole ratio within the range of 3–6. Typical space velocities (WHSV) will range from about 1.3 to about $3hr^{-1}$. In the plant operations described hereafter space velocites ranging from about 1.1 to $1.9hr^{-1}$ provided toluene conversion at about 80% of theory. At those space velocities the nonaromatic product yield was usually less than 1%.

As further described in the aforementioned Butler et al application, a hot inert gas such as hydrogen may be used in a preflush procedure in order to dehydrate the mordenite catalyst and remove water which is believed to function within the catalyst framework to block active sites. The preflush may be carried out with gas heated to a temperature of about 400° C. and continued for a period of one day or more. As also noted in the Butler et al application, the toluene feed may contain water in excess of the 15 ppm concentration indicated by the aforementioned patent by Pollitzer to be unsatisfactory, and well above the 25 ppm upper limit disclosed by Pollitzer. Thus, water concentrations ranging from about 50 ppm up to 250 ppm (saturation) encountered in toluene feedstocks under ambient conditions can be tolerated. For a further description of the process parameters and procedures which may be employed in toluene disproportionation processes conducted in accordance with the present invention, reference is made to the aforementioned application Ser. No. 826,848 to Butler et al, the entire disclosure of which is incorporated herein by reference.

As noted previously, it is a conventional practice of disproportionation processes to co-feed hydrogen to the disproportionation reactor. While as indicated by reaction (1), hydrogen is not theoretically involved in the disproportionation reaction, in practice substantial quantities of hydrogen are normally consumed. When employing high silica/alumina ratio mordenite catalysts as taught in the aforementioned application Ser. No. 826,848 by Butler et al, hydrogen used in commercial processes can then be kept to a value of less than 0.1 mol of hydrogen per mol of toluene. Thus, the amount of hydrogen withdrawn from the reaction zone in relation to the amount of hydrogen co-feed is such as to provide an average consumption of less than 0.1 mol of hydrogen per mol of toluene.

In the present invention hydrogen, co-feed is supplied to the disproportionation reaction zone which contains an aluminum deficient mordenite catalyst, i.e., one having a silica/alumina mol ratio of at least 30, as described in the aforementioned Butler et al application. As the toluene feedstock and hydrogen co-feed are supplied to the reaction zone, the disproportionation product, principally benzene, xylene, and unreacted toluene and small amounts of heavy aromatics and nonaromatics, is withdrawn from the reaction zone. At one or more points during the life of the catalyst, that is, before regeneration, the supply of toluene feedstock to the reaction zone is interrupted, thus shutting down the disproportionation process. During at least a portion of the shutdown time, preferably at least one day and typically several days or more, the supply of hydrogen to the reaction zone is continued along with the withdrawal of hydrogen from the reaction zone. Normally hydrogen introduction and withdrawal will continue throughout the shutdown period. However, if the reactor is shutdown for a prolonged period of time, e.g. weeks or months, hydrogen injection may be terminated and the reactor sealed off to maintain the catalyst in the reactor under a hydrogen environment. In this case the reactor may be allowed to cool down with time but the hydrogen pressure normally should be maintained at a value of about at least 100 psig of static pressure.

Preferably, hydrogen supply to and withdrawal from the reaction zone during the shutdown period is continued for a duration of at least 3 days. Thereafter, if a longer shutdown time of the disproportionation unit is desired, the reactor may be sealed as described above to maintain the mordenite catalyst under a hydrogen environment. It is also preferred, during the hydrogen flushing step, to introduce the hydrogen into the reactor at a rate to provide a space velocity based upon the mordenite catalyst within the range of 12–45 scf of hydrogen per pound of catalyst per hour.

The foregoing interrupt procedure may be repeated one or more times at a regular or irregular intervals. Normally, whenever the disproportionation unit is shutdown such as for maintenance and the like, hydrogen injection should be continued to flush the catalyst bed during the shutdown period. The invention results in an increase of the efficiency of the catalyst when the disproportionation unit is brought back upstream, as indicated by the relationship between the amount of toluene converted and the reaction temperature, and improves the aging quality of the catalyst, that is, it increases the life of the catalyst before regeneration is required.

The advantages accruing from the practice of the present invention are illustrated by data obtained from plant operations. Tables I–V illustrate such process data taken at a toluene disproportionation plant operated over a period of several hundred days. The catalyst employed in the plant operation was the aluminum deficient mordenite catalyst identified in the aforementioned Butler et al application as catalyst C and having a silica/alumina ratio of 48. The process was operated in accordance with the procedure described in Butler et al wherein the reaction temperature was progressively increased with the age of the catalyst on stream. Hydrogen cofeed was supplied along with the toluene feed to provide a hydrogen/toluene mole ratio of about 4 or more. The hydrogen partial pressure within the reactor ranged from about 585 to 650 psig.

TABLE I

| | Days on Line | | | | | | |
|---|---|---|---|---|---|---|---|
| | 76 | 77 | 78 | 79 | 82 | 83 | 84 |
| Feed Rate | 4000 | 4040 | 1334 | 1883 | 2683 | 4000 | 4514 |
| % Tol | 99.73 | 89.83 | 99.88 | 99.99 | 99.89 | 99.84 | 99.99 |
| Temp °F. | | | | | | | |
| In | 761 | 757 | 547 | 708 | 655 | 773 | 782 |
| Out | 780 | 783 | 552 | 723 | 647 | 788 | 802 |
| Product, % | | | | | | | |
| Non-Aro | .01 | .01 | .01 | .01 | | .14 | .04 |
| Benz | 17.05 | 15.9 | 15.12 | 6.12 | | 7.73 | 17.09 |
| Tol | 58.9 | 59.67 | 58.23 | 57.33 | | 56.40 | 55.98 |
| EB | .66 | .57 | 1.01 | 1.17 | | 1.31 | .84 |
| PX | 5.42 | 5.26 | 5.65 | 5.57 | | 5.93 | 5.51 |
| MX | 10.76 | 10.3 | 11.23 | 11.0 | | 11.66 | 11.12 |
| OX | 5.28 | 5.1 | 5.39 | 5.52 | | 5.97 | 5.46 |
| $C_9+$ | 1.99 | 3.47 | 3.4 | 3.29 | | .89 | 3.52 |

TABLE II

| | Days on Line | | | | | |
|---|---|---|---|---|---|---|
| | 94 | 95 | 96 | 99 | 100 | 101 |
| Feed Rate | 6512 | 5903 | 3057 | 5230 | 6470 | 6882 |
| % Tol | 58.01 | 59.91 | 56.9 | 58.83 | 59.1 | 61.53 |
| Temp °F. | | | | | | |
| In | 805 | 803 | 770 | 784 | 785 | 790 |
| Out | 821 | 817 | 784 | 796 | 811 | 814 |
| Product, % | | | | | | |
| Non-Aro | .25 | .2 | .25 | .02 | .03 | .06 |
| Benz | 16.09 | 16.18 | 18.4 | 15.1 | 16.04 | 16.01 |
| Tol | 58.01 | 59.91 | 56.9 | 60.03 | 59.1 | 61.53 |
| EB | .65 | .58 | .9 | .84 | .75 | .68 |
| PX | 5.28 | 5.27 | 5.9 | 5.47 | 5.37 | 5.34 |
| MX | 10.46 | 10.47 | 11.2 | 10.56 | 10.52 | 10.3 |
| OX | 5.24 | 5.23 | 5.8 | 5.29 | 5.33 | 5.18 |
| $C_9+$ | 3.8 | 1.77 | 1.1 | 2.6 | 3.94 | .94 |

TABLE III

| | Days on Line | | | | |
|---|---|---|---|---|---|
| | 143 | 144 | 160 | 161 | 162 |
| Feed Rate | 6995 | 6506 | 2094 | 6372 | 6509 |
| % Tol | 79.78 | 99.86 | 99.8 | 99.8 | 97.6 |
| Temp °F. | | | | | |
| In | 816 | 808 | 742 | 798 | 813 |
| Out | 835 | 826 | 726 | 821 | 831 |
| Product, % | | | | | |
| Non-Aro | .04 | .03 | | .05 | .07 |
| Benz | 16.05 | 16.6 | | 15.3 | 16.6 |

TABLE III-continued

| | Days on Line | | | | |
|---|---|---|---|---|---|
| | 143 | 144 | 160 | 161 | 162 |
| Tol | 59.26 | 58.6 | | 58.6 | 58.5 |
| EB | .54 | .59 | | .6 | .53 |
| PX | 4.98 | 5.3 | | 5.46 | 5.2 |
| MX | 9.9 | 10.4 | | 11.63 | 11.3 |
| OX | 4.98 | 5.2 | | 5.4 | 5.1 |
| $C_9+$ | 4.25 | 3.28 | | 3.0 | 2.7 |

TABLE IV

| | Days on Line | | | | | |
|---|---|---|---|---|---|---|
| | 228 | 229 | 230 | 232 | 239 | 240 |
| Feed Rate | 5672 | 6108 | 3086 | 3021 | 4156 | 4919 |
| % Tol | 99.55 | 99.61 | 99.27 | 96.34 | 89.67 | 97.93 |
| Temp °F. | | | | | | |
| In | 825 | 825 | 805 | 808 | 812 | 807 |
| Out | 848 | 848 | 826 | 821 | 833 | 836 |
| Product, % | | | | | | |
| Non-Aro | .05 | .3 | | .07 | .1 | .1 |
| Benz | 16.24 | 15.7 | 14.55 | 16.19 | 14.3 | 13.1 |
| Tol | 57.58 | 58.3 | 58.10 | 55.38 | 57.1 | 57.4 |
| EB | .62 | .6 | .61 | .90 | .95 | .83 |
| PX | 5.45 | 5.37 | 5.68 | 5.71 | 5.79 | 6.0 |
| MX | 11.9 | 11.78 | 12.37 | 12.62 | 12.5 | 13.1 |
| OX | 5.42 | 5.36 | 5.67 | 5.62 | 5.78 | 6.0 |
| $C_9+$ | 2.76 | 2.68 | 2.68 | 3.51 | 3.7 | 3.4 |

TABLE V

| | Days on Line | | | | | | | |
|---|---|---|---|---|---|---|---|---|
| | 252 | 253 | 257 | 258 | 259 | 260 | 261 | 262 |
| Feed Rate | 4323 | 3769 | 3844 | 4383 | 4668 | 3999 | 4409 | 4659 |
| % Tol | 99.32 | 99.47 | 98.26 | 99.49 | 98.90 | 99.85 | | 99.29 |
| Temp °F. | | | | | | | | |
| In | 819 | 809 | 813 | 816 | 817 | 814 | 835 | 834 |
| Out | 839 | 835 | 830 | 833 | 834 | 835 | 855 | 859 |
| Product, % | | | | | | | | |
| Non-Aro | .02 | .06 | .14 | .09 | .09 | .09 | .06 | .06 |
| Benz | 17.15 | 16.84 | 16.19 | 17.62 | 16.5 | 16.7 | 16.61 | 17.24 |
| Tol | 54.75 | 56.4 | 55.24 | 57.04 | 57.8 | 54.5 | 54.5 | 54.46 |
| EB | .98 | .72 | .69 | 8.5 | .60 | .9 | .95 | .77 |
| PX | 5.8 | 5.54 | 5.43 | 5.4 | 5.34 | 5.88 | 5.92 | 5.81 |
| MX | 12.4 | 11.83 | 11.85 | 11.7 | 11.65 | 12.73 | 12.8 | 12.48 |
| OX | 5.65 | 5.45 | 5.38 | 5.34 | 5.28 | 5.82 | 5.9 | 5.79 |
| $C_9+$ | 3.47 | 3.18 | 4.6 | 3.1 | 2.76 | 3.38 | 3.3 | 3.41 |

TABLE VI

| | BEFORE SHUTDOWN | | | Down Time | AFTER SHUTDOWN | | |
|---|---|---|---|---|---|---|---|
| Table | T °F. | Bbl/d | % Conv | Days | °F. | Bbl/d | Conv |
| I | 783 | 4000 | 40 | 6 | 788 | 4000 | 43 |
| II | 805 | 6512 | 42 | 4 | 784 | 6470 | 42 |
| III | 808 | 6507 | 41 | 18 | 813 | 6509 | 42 |
| IV | 805 | 3886 | 42 | 7 | 812 | 4156 | 44 |
| V | 817 | 4668 | 42 | 3 | 834 | 4659 | 46 |

Tables I–V present data obtained for periods immediately before and immediately after shutdown of the reactor. Each Table presents an average, on a daily basis, of the inlet and outlet temperature, the feed rate in barrels per day of the toluene feedstock, the percent toluene in the feedstock, and an analysis of the hydrocarbon product from the disproportionation reactor. The elapsed time in days since the initial startup of the disproportionation reactor is given at the head of each Table. Thus, by way of an exemplary description of the data presented, in Table I at days 76 and 77 the toluene feedstock was supplied to the reactor at average daily rates of about 4000 and 4040 barrels per day. Starting with day 78, the reactor started into a shutdown mode as evidenced by the decreased feed rate and during days 80 and 81 the reactor was completely shutdown except for the continued injection of hydrogen. The hydrogen introduced into the reactor during the shutdown period was preheated at a temperature of about 260° C. and the temperature within the reactor decreased somewhat with continued hydrogen introduction and withdrawal. By the time the reactor was started to be brought back to stream, the reactor temperature had declined to about 650° F. as indicated in Table I under day 82. The shutdown procedure with continued hydrogen production was repeated four times as indicated in Tables II–V. At one other time, not reported in the Tables but occurring between the data the intervals covered by Tables III and IV the reactor was shutdown for about 14 days without the continued supply of hydrogen.

Table VI presents an overview of the toluene disproportionation process immediately before and immediately after shutdown for each of the shutdown intervals depicted in Tables I–V. In Table VI, the second, third and fourth columns indicate the temperature at the reactor outlet, feed rate and percent toluene conversion observed immediately before shutdown. The fifth column indicates the shutdown time including periods of substantially reduced feed rates involved in shutting down the reactor and bringing it up to normal operation. As indicated previously, the hydrogen was continuously injected and withdrawn to provide sustained flushing of the catalyst at a temperature of about 250° C. or above. The last three columns in Table VI present the reactor outlet temperature, the feed rate and the average toluene conversion observed after the reactor was returned to stream.

As can be seen from an examination of Table VI, in most cases upon restarting the reactor, somewhat higher toluene conversion rates were achieved with little increase in temperature. At the conclusion of the shutdown period for Table II, the conversion remained at 42% even though the reactor temperature decreased by about 20° F.

A possibly more significant advantage of the invention is the influence of the hydrogen flushing step on the aging quality of the catalyst. This is illustrated by the drawing which is a graph of the reactor inlet temperature T, in ° F. on the ordinate versus the elapsed time E in days on the abscissa for the disproportionation unit from which the data of Tables I–VI were obtained. In the drawing, the data points for curve 1 indicate the actual reactor inlet temperature observed during plant operations. Further in the drawing, curve 2 represents a projection of the average operating temperature derived from the first three months of operation necessary to achieve the desired toluene conversion of about 80% of theoretical (corresponding to an actual toluene conversion of about 42%). As indicated in the aforementioned patent application to Butlet et al, the operating temperature can be expected to increase as the catalyst becomes less active with age. However, as shown by the actual data points in the drawing, the operating after the repeated hydrogen flushing steps, rose only moderately with time, and the average daily temperature fell well below that projected by curve 2. Also, each of the shutdown periods during which hydrogen was injected was followed by a temperature plateau, indicating a beneficial action of the hydrogen flushing step.

Having described specific embodiments of the present invention, it will be understood that modification thereof may be suggested to those skilled in the art, and it is intended to cover all such modifications as fall within the scope of the appended claims.

We claim:

1. In a process for the disproportionation of a toluene containing feedstock to produce a disproportionation product containing benzene and xylene, the steps comprising:
    (a) supplying said toluene feedstock to a reaction zone into contact with a mordenite catalyst within said reaction zone having a silica/alumina mole ratio of at least 30;
    (b) co-feeding hydrogen to said reaction zone to provide a hydrogen environment therein;
    (c) operating said reaction zone under temperature and pressure conditions to effect the disproportionation of toluene to benzene and xylene;
    (d) withdrawing said disproportionation product containing benzene and xylene from said reaction zone;
    (e) interrupting the supply of said toluene feedstock into said reaction zone; and
    (f) subsequent to interrupting the supply of toluene feedstock to said reaction zone supplying hydrogen to said reaction zone and withdrawing hydrogen from said reaction zone.

2. The method of claim 1 wherein subsequent to step (f), the toluene feedstock is again supplied to said reaction zone to reinstate said disproportionation process and thereafter repeating steps (e) and (f).

3. The method of claim 1 wherein hydrogen is supplied to said reaction zone in step (f) at a rate to provide a hydrogen space velocity relative to said catalyst within the range of 12–45 scf of hydrogan per pound of catalyst per hour.

4. The method of claim 1 wherein hydrogen is supplied to and withdrawn from said reaction zone in step (f) for a period of at least one day and thereafter reinstating the supply of said toluene feedstock to said reaction zone.

5. The method of claim 4 wherein hydrogen is supplied to said reaction zone in step (f) for a period of at least 3 days.

6. The method of claim 1 wherein said reaction zone is operated at a temperature within the range of 370°–500° C. during the supply of said toluene feedstock to said reaction zone and is maintained at a temperature of at least 250° C. during the supply of hydrogen to and withdrawal of hydrogen from said reaction zone.

7. The method of claim 1 wherein said mordenite catalyst has a silica/alumina mole ratio within the range of 40–60.

8. The method of claim 1 wherein said mordenite catalyst has a silica/alumina mole ratio of about 48.

9. The method of claim 1 wherein hydrogen supply to and withdrawal from said reaction zone in step (f) is terminated and thereafter said reaction zone is maintained under a hydrogen pressure of at least 100 psig to provide a hydrogen environment for said mordenite catalyst.

10. The method of claim 9 further comprising the step of thereafter starting the injection of said toluene feedstock and hydrogen to reinstitute said disproportionation process.

* * * * *